US007956208B2

(12) United States Patent
Du Preez

(10) Patent No.: US 7,956,208 B2
(45) Date of Patent: Jun. 7, 2011

(54) PREPARATION OF PLATINUM (II) COMPLEXES

(75) Inventor: Jan Gysbert Hermanus Du Preez, Port Elizabeth (ZA)

(73) Assignee: Platco Technologies (Proprietary) Limited, Port Elizabeth (ZA)

(*) Notice: Subject to any disclaimer, the term of this patent is extended or adjusted under 35 U.S.C. 154(b) by 268 days.

(21) Appl. No.: 12/162,745

(22) PCT Filed: Jan. 30, 2007

(86) PCT No.: PCT/IB2007/000213
§ 371 (c)(1),
(2), (4) Date: Nov. 4, 2008

(87) PCT Pub. No.: WO2007/085957
PCT Pub. Date: Aug. 2, 2007

(65) Prior Publication Data
US 2009/0281319 A1 Nov. 12, 2009

Related U.S. Application Data

(60) Provisional application No. 60/762,871, filed on Jan. 30, 2006.

(51) Int. Cl.
*C07F 15/00* (2006.01)
(52) U.S. Cl. .............................. 556/137; 548/106; 546/6
(58) Field of Classification Search .................. 556/137; 548/106; 546/6
See application file for complete search history.

(56) References Cited

U.S. PATENT DOCUMENTS

| | | | |
|---|---|---|---|
| 4,169,846 A | 10/1979 | Kidani et al. |
| 4,536,571 A | 8/1985 | Stockel et al. |
| 5,281,447 A | 1/1994 | Brady et al. |
| 5,290,961 A | 3/1994 | Okamoto et al. |
| 5,338,874 A | 8/1994 | Nakanishi et al. |
| 5,420,319 A | 5/1995 | Okamoto et al. |
| 5,716,988 A | 2/1998 | Ibrahim et al. |
| 5,959,133 A | 9/1999 | Ohnishi |
| 6,376,057 B1 | 4/2002 | Akao et al. |
| 6,866,857 B1 | 3/2005 | Mauvernay |
| 7,070,796 B1 | 7/2006 | Ibrahim et al. |
| 7,122,668 B2 | 10/2006 | Barenholz et al. |
| 7,208,616 B2 | 4/2007 | Menez et al. |
| 7,309,796 B2 | 12/2007 | Pepels et al. |
| 7,351,846 B2 | 4/2008 | Zák et al. |
| 2004/0186172 A1 | 9/2004 | Ibrahim |
| 2006/0063833 A1 | 3/2006 | Schridde et al. |
| 2006/0275331 A1 | 12/2006 | Zaludek et al. |
| 2007/0073074 A1 | 3/2007 | Zak et al. |
| 2007/0167643 A1 | 7/2007 | Du Preez |
| 2007/0197811 A1 | 8/2007 | Menez et al. |
| 2008/0064895 A1 | 3/2008 | Du Perez |
| 2009/0299085 A1 | 12/2009 | Du Preez |
| 2009/0312417 A1 | 12/2009 | Du Preez |

FOREIGN PATENT DOCUMENTS

| | | |
|---|---|---|
| EP | 0 115 929 A1 | 8/1984 |
| EP | 0 345 356 A1 | 12/1989 |
| EP | 0 345 356 A4 | 12/1989 |
| EP | 0 567 438 B1 | 10/1993 |
| EP | 0 617 043 B1 | 9/1994 |
| EP | 0 625 523 B1 | 11/1994 |
| EP | 0 715 854 B1 | 6/1996 |
| EP | 0 774 963 B1 | 5/1997 |
| EP | 0 801 070 B1 | 10/1997 |
| EP | 0 881 226 B1 | 12/1998 |
| EP | 0 943 331 B1 | 9/1999 |
| EP | 1 121 117 B1 | 8/2001 |
| EP | 1 207 875 B1 | 5/2002 |
| EP | 1 308 453 A2 | 5/2003 |
| EP | 1 308 453 A3 | 5/2003 |
| EP | 1 308 454 B1 | 5/2003 |
| EP | 1 561 754 B1 | 8/2005 |
| EP | 1 680 434 B1 | 7/2006 |
| EP | 1 704156 | 9/2006 |
| GB | 2 210 039 A | 6/1989 |
| JP | 61-0229893 | 10/1986 |
| JP | 5-301884 A | 11/1993 |
| JP | 09-040685 | 2/1997 |
| JP | 09-278785 | 10/1997 |
| JP | 10-095793 | 4/1998 |
| WO | WO-03/004505 A1 | 1/2003 |
| WO | WO-2005/051966 A1 | 6/2005 |
| WO | WO-2005/075489 A1 | 8/2005 |
| WO | WO-2006/023154 A1 | 3/2006 |
| WO | WO-2006/024897 A1 | 3/2006 |
| WO | WO-2006/108428 A1 | 10/2006 |

OTHER PUBLICATIONS

Bierbach, U. et al. (1998, e-pub. Jan. 31, 1998). "Modification of Platinum(II) Antitumor Complexes with Sulfur Ligands. 1. Synthesis, Structure, and Spectroscopic Properties of Cationic Complexes of the Types [PtCl(diamine)(L)]NO$_3$ and [{PtCl(diamine)}$_2$(L-L)](NO$_3$)$_2$ (L= Monofunctional Thiourea Derivative; L-L= Bifunctional Thiourea Derivative)," *Inorg. Chem.* 37(4):708-716. Database CA [Online] Chemical Abstracts Service, Columbus, Ohio, US; Abel, Edward W. et al: "Platinum metal complexes of potentially chelating alkene thioether and selenoether ligands: the synthesis and dynamic nuclear magnetic resonance study of [MX2{E[(CH2)nCR:CR2]2}] (M-Pt or Pd; X=Cl, Br, or I; E=S or Se; n=2 or 3; R=H or Me) and the x-ray crystal structure of cis-diiodo(5-thi" retrieved from STN Database accession No. 1990:235576, Journal of the Chemical Society, Dalton Transactions: Inorganic Chemistry (1972-1999) (11):2315-2321, CODEN: JCDTBI; ISSN: 0300-9246, 1989 (Abstract only).

(Continued)

*Primary Examiner* — Porfirio Nazario Gonzalez
(74) *Attorney, Agent, or Firm* — Morrison & Foerster LLP

(57) ABSTRACT

This invention relates a method for the preparation of platinum(II) oxalato complexes from their dihalogenoplatinum (II) precursors having either neutral monodentate or bidentate non-leaving co-ligands. Of particular interest is oxaliplatin. The method includes the step of reacting a halogenoplatinum (II) complex containing a neutral monodentate or bidentate ligand with an oxalate in a non-aqueous solvent or a mixed solvent system. The mixed solvent system is solvent mixture containing a non-aqueous solvent and water. According to the present invention, the non-aqueous solvent is an alcohol.

38 Claims, No Drawings

OTHER PUBLICATIONS

Database CA [Online] Chemical Abstracts Service, Columbus, Ohio, US; Abel, Edward W. et al: "Platinum metal complexes of potentially chelating alkene-thioether and alkene-selenoether ligands: synthesis and dynamic nuclear magnetic resonance study of [MX2{MeE(CH2)nCH=CH2}] (M= platinum or palladium; X=Cl, Br, or I; E=S or Se; n=2 or 3) and the x-ray structure of cis-dibromo(2-thia-6-heptene)platinum(II)," retrieved from STN Database accession No. 1990:56232, Journal of the Chemical Society, Dalton Transactions: Inorganic Chemistry (1972-1999) 11:2315-2321, CODEN: JCDTBI; ISSN: 0300-9246, 1989 (Abstract only).

Database CA [Online] Chemical Abstracts Service, Columbus, Ohio, US; Abel, Edward W. et al: "Synthetic, dynamic nuclear magnetic resonance and crystallographic studies of platinum complexes containing silyl-substituted dialkenyl-thioether and -selenoether ligands," retrieved from STN Database accession No. 1995:114833, abstract, compound I & Journal of the Chemical Society, Dalton Transactions: Inorgamic Chemistry (1972-1999) 18:2637-2643, CODEN: JCDTBI; ISSN: 0300-9246, 1994 (Abstract only).

Database CA [Online] Chemical Abstracts Service, Columbus, Ohio, US; Balakrishna, Maravanji S. et al: "Heterodifunctional ligands derived from monooxidized bis(phosphino)amines. Synthesis and transition metal (molybdenum(O), tungsten(O), rhodium(I), palladium(II), and platinum(II)) complexes of (diphenylphosphino)(diphenylphosphinothio lyl)- and (diphenylphosphino)(diphenylphosphinoselen oyl)phenylam," retrieved from STN Database accession No. 1993:685076, abstract & Inorganic Chemistry 32(25):5676-5681, CODEN: INOCAJ; ISSN: 0020-1669, 1993 (Abstract only).

Database CA [Online] Chemical Abstracts Service, Columbus, Ohio, US; Belletti, Daniele et al: "Reactivity of Ph2(2-C5H4N)Pse towards Ru3(CO)12 and mononuclear MCl2(PhCN)2 (M=Pd or Pt) complexes," retrieved from STN Database accession No. 2003:483190, Inorganica Chimica Acta 350:421-427, CODEN: ICHAA3; ISSN: 0020-1693, 2003 (Abstract only).

Database CA [Online] Chemical Abstracts Service, Columbus, Ohio, US; Bhasin, Kuldip K. et al: "2,5-Diselena-3,3,4,4-tetrafluorohexane and 2,5-diselena-1,1,1,6,6,6- hexafluorohexane and their platinum and palladium chloride complexes," retrieved from STN Database accession No. 1979:567640, Journal of Fluorine Chemistry 14(2):171-176, CODEN: JFLCAR; ISSN: 0022-1139, 1979 (Abstract only).

Database CA [Online] Chemical Abstracts Service, Columbus, Ohio, US; Clarke, M. L. et al: "First examples of M-Se-P-N-N heterocycles," retrieved from STN Database accession No. 2001:237332, Inorganic Chemistry Communications 4(3):115-118, CODEN: ICCOFP; ISSN:1387-7003, 2001 (Abstract only).

Database CA [Online] Chemical Abstracts Service, Columbus, Ohio, US; Harbron, Stephen K. et al: "Coordination chemistry of higher oxidation states. Part 24. Palladium(IV) and nickel(III) complexes of hybrid thio- and seleno-ether ligands," retrieved from STN Database accession No. 1987:589472, Inorganica Chimica Acta 130(1):43-47, CODEN: ICHAA3; ISSN: 0020-1693, 1987 (Abstract only).

Database CA [Online] Chemical Abstracts Service, Columbus, Ohio, US; Kemmitt, Tim et al: "Chelating ditelluroether complexes of palladium and platinum: synthesis and multinuclear NMR studies. Structure of dibromo(meso-1,3-bis(phenyltelluro)propane )palladium(II): [Pd{meso-PhTe(CH2)3TePh}Br2]," retrieved from STN Database accession No. 1989:87401, Inorganic Chemistry 28(4):692-696, CODEN: INOCAJ; ISSN: 0020-1669, 1989 (Abstract only).

Database CA [Online] Chemical Abstracts Service, Columbus, Ohio, US; Khanna, Anju et al: "Synthesis and multinuclear NMR studies of 3-aminopropyl(aryl)chalcogenides, NH2CH2CH2CH2Ear (E=Se, Te), and their complexes with Pt(II) and Pd(II)," retrieved from STN Database accession No. 1995:569289. Journal of Organometallic Chemistry 494(1-2):199-204, CODEN: JORCAI; ISSN:0022-328X, 1995 (Abstract only).

Database CA [Online] Chemical Abstracts Service, Columbus, Ohio, US; Khuzaie, Rula F. et al: "Screening for anticomplementary activity of some platinum (II) and palladium (II) complexes with various donor ligands and anions," XP002317068 retrieved from STN Database accession No. 2002:445382, Oriental Journal of Chemistry 18(1):1-6, CODEN: OJCHEG; ISSN: 0970- 020X, 2002 (Abstract only).

Database CA [Online] Chemical Abstracts Service, Columbus, Ohio, US; Knorr, Michael et al: "Synthesis and molecular structures of platinum and mercury complexes chelated by (phenylthiomethyl)silane ligands," retrieved from STN Database accession No. 2004:973319, Zeitschrift Fuer Anorganische Und Allegemeine Chemie 630(12):1955-1961, CODEN: ZAACAB; ISSN: 0044-2313, Oct. 21, 2004 (Abstract only).

Database CA [Online] Chemical Abstracts Service, Columbus, Ohio, US; Mizuno, Masagi: "Linear chain compound bisoxalatoplatinate complexes," XP002317074 retrieved from STN Database accession No. 1989:432596, Kagaku Kogyo Shiryo (Tsukuba, Japan) 23(5):201-216, CODEN: KKSHEP; ISSN: 0288-8882, 1989 (Abstract only).

Database CA [Online] Chemical Abstracts Service, Columbus, Ohio, US; Prignano, Andrea L. et al: "Silica-anchored bis(trialkylphosphine) platinum oxalate: a photogenerated catalyst for olefin hydrosilation," XP002317070 retrieved from STN Database accession No. 1987:77537, Monatshefte Fuer Chemie 117(5):617-619, CODEN: MOCMB7; ISSN: 0026-9247, 1986 (Abstract only).

Database CA [Online] Chemical Abstracts Service, Columbus, Ohio, US; Puniyani, Sushil et al: "Platinum (II) complexes of cyclohexanone and cyclopentanone thiosemicarbazones," XP002317071 retrieved from STN Database accession No. 1985:447222 Indian Journal of Chemistry, Section A: Inorganic, Physical, Theoretical & Analytical 24a(3):240-241, CODEN: IJCADU; ISSN: 0376-4710,1985 (Abstract only).

Database CA [Online] Chemical Abstracts Service, Columbus, Ohio, US; Rashan, Luay J. et al: "In vitro antitumor activity of platinum (II) complexes with various nitrogen containing ligands," XP002317069 retrieved from STN Database accession No. 1998:522331, Biologia (Bratislava) 53(3):349-352, CODEN: BLOAAO; ISSN: 0006-3088, 1998 (Abstract only).

Database CA [Online] Chemical Abstracts Service, Columbus, Ohio, US; Song, Rita et al: "Synthesis and selective tumor targeting properties of water soluble porphyrin-Pt(II) conjugates," [Erratum to document cited in CA137:362598] XP002317067 retrieved from STN Database accession No. 2002:85473, Journal of Inorganic Biochemistry 92(3-4):200, CODEN: JIBIDJ; ISSN: 0162-0134, 2002. Erratum found in Database CA [Online] Chemical Abstracts Service, Columbus, Ohio, US; Song, Rita et al: "Synthesis and selective tumor targeting properties of water soluble porphyrin-Pt(II) conjugates," retrieved from STN Database accession No. 2002:249587 Journal of Inorganic Biochemistry 89(1-2):83-88, CODEN: JIBIDJ; ISSN: 0162-0134, 2002 (Abstract only).

Database CA [Online] Chemical Abstracts Service, Columbus, Ohio, US; Syamal, A. et al: "Synthesis of new platinum (II) complexes with ethanethiolamine, o-aminothiophenol and bidentate carboxylic acids," XP002317072 retrieved from STN Database accession No. 1983: 209058, Revue De Chimie Minerale 20(1):123-128, CODEN: RVCMA8; ISSN: 0035-1032, 1983 (Abstract only).

Database CA [Online] Chemical Abstracts Service, Columbus, Ohio, US; Uttecht, J.-G. et al: "Synthesis, vibrational spectra and normal coordinate analysis of (n-Bu4N)2 [Pt(SCN)n(ox)], n=2, 4, and crystal structure of [(C5H5N)2CH2][Pt(SCN)4(ox)]," XP002317073 retrieved from STN Database accession No. 2002:781520, Zeitschrift Fuer Naturforschung, B: Chemical Sciences 57(9):1036-1042, CODEN: ZNBSEN; ISSN: 0932-0776, 2002 (Abstract only).

Gladiali, S. et al. (1988). "Synthesis, Structure, and Dynamic Behaviour of Transition Metal Chelate Complexes with Atropismeric Dithioether Ligands" *Eur. J. Inorg. Chem.* pp. 113-118.

Gümüs, F. et al. (2003). "Synthesis, Characterization and In Vitro Cytotoxic, Mutagenic and Antimicrobial Activity of Platinum(II) Complexes with Substituted Benzimidazole Ligands," *J. Inorg. Biochem.* 94(3):255-262.

International Preliminary Report on Patentability mailed on Nov. 23, 2005, for PCT Patent Application No. PCT/IB2004/003855 filed Nov. 24, 2003, 20 pages.

International Preliminary Report on Patentability mailed on Mar. 1, 2007, for PCT Patent Application No. PCT/IB2005/000570, filed Mar. 7, 2005, 28 pages.

International Preliminary Report on Patentability mailed on Aug. 5, 2008, for PCT Patent Application No. PCT/IB2007/000213, filed Jan. 30, 2007, 6 pages.

International Search Report mailed on Mar. 23, 2005, for PCT Patent Application No. PCT/IB2004/003855, filed Nov. 24, 2004, 5 pages.

International Search Report mailed on Aug. 2, 2005, for PCT Patent Application No. PCT/IB2005/000570, filed Mar. 7, 2005, 7 pages.

International Search Report mailed on Jun 11, 2007, for PCT Patent Application No. PCT/IB2007/000213, filed Jan. 30, 2007, 2 pages.

Khokhar, A.R. et al. (1985). "The Synthesis and Antitumor Properties of a Series of Water Soluble Carboxylato-(1,2-diaminocyclohexane) Platinum(II) Complexes", *Inorganica Chimica Acta* 108:63-66.

Mizuno, M. (1988). "Linear Chain Compound Bisoxalatoplatinate Complexes," *Kagaku Kogyo Shiryo* 23(5):201-216. (Japanese language only.).

Pasini, A. et al. (1989). "A New Synthetic Method for Diaminomalonatoplatinum Type Complexes and the Unexpected Behavior of [PtCl$_2$(trans-dach)]," *Inorganic Chemical* 152, Italy (1988), pp. 19-20.

Puniyani, S. et al. Platinum(II) Complexes of Cyclohexanone and Cyclopentanone Thiosemicarbazones, *India Journal of Chemistry, Section A: Inorganic, Physical, Theoretical & Analytical* 24A(3):240-241, (1985).

Reedijk, J. (1999, e-pub. Aug. 21, 1999). "Why Does Cisplatin Reach Guanine-N7 with Competing S-Donor Ligands Available in the Cell?" *Chem. Rev.* 99(9):2499-2510.

Schanz, H-J., et al. (2003). "Improved Resolution Methods for (*R,R*)- and (*S,S*)-cyclohexane-1,2-diamine and (*R*)- and (*S*)-BINOL", *Tetrahedron: Asymmetry* 14(18):2763-2769.

Shriver, D.F., ed. (1979). "Partially Oxidized Potassium Bis(oxalate)palatinate," *Inorganic Syntheses*, vol. 19, John Wiley and Sons: New York, NY, one page.

Thornber, C.W. (1979). "Isosterism and Molecular Modification in Drug Design," *Chemical Society Reviews* [Chemical Society, London, GB] 8(4):563-580.

Written Opinion mailed on mailed on Mar. 21, 2006, for PCT Patent Application No. PCT/IB2004/003855, filed on Nov. 24, 2004, 12 pages.

Written Opinion mailed on Mar. 1, 2007, for PCT Patent Application No. PCT/IB2005/000570, filed on Mar. 7, 2005, 10 pages.

Written Opinion mailed on Aug. 5, 2008, for PCT Patent Application No. PCT/IB2007/000213, filed on Jan. 30, 2007, 5 pages.

Syamal, A et al. (Dec. 20, 1982). "Platinum (II and IV) Complexes with NS and No Donor Ligands," *Current Science* 51(24):1153-1155.

PREPARATION OF PLATINUM (II) COMPLEXES

CROSS-REFERENCE TO RELATED APPLICATIONS

This application is a National Phase filing under 35 U.S.C. §371 of International Application No. PCT/IB2007/000213 filed on Jan. 30, 2007, which claims priority to U.S. Provisional Application No. 60/762,871 filed on Jan. 30, 2006. The contents of these applications are hereby incorporated by reference in their entireties.

BACKGROUND OF THE INVENTION

This invention relates to the preparation of platinum(II) oxalato complexes from their dihalogenoplatinum(II) precursors having either neutral monodentate or bidentate non-leaving co-ligands. Of particular interest is cis-oxalato(trans-l-1,2-cyclohexanediamine)platinum(II) (also known as oxaliplatin), which has become increasingly important due to its anticancer activity.

Dicarboxylatoplatinum(II) complexes (such as oxaliplatin) containing a neutral bidentate ligand ("non-leaving group") have in the past been synthesized by way of a process that utilizes a silver salt to remove halide ions from the complex. The use of a silver compound in the process results in numerous contaminants, which must be removed by further processes in order to achieve a purity that is suitable for anticancer pharmaceutical agent purposes.

Oxaliplatin and its pharmaceutical properties were first disclosed by Kidani et al. in J Med Chem, 1978, 21, 13135 and in U.S. Pat. No. 4,169,846. In this patent, a halogenoplatinum compound is used as the starting material. Halide ions are removed by a silver salt, whereafter an oxalate is introduced, either as the free acid or a salt thereof.

In general, a method for the production of oxaliplatin is as set out below:

Step 1.

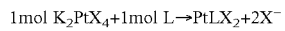

1mol $K_2PtX_4$ + 1mol L → $PtLX_2$ + $2X^-$

X=Cl, Br, I and L=trans-l-1,2-diaminocyclohexane

Step 2.

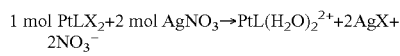

1 mol $PtLX_2$ + 2 mol $AgNO_3$ → $PtL(H_2O)_2^{2+}$ + 2AgX + $2NO_3^-$ or

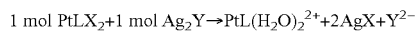

1 mol $PtLX_2$ + 1 mol $Ag_2Y$ → $PtL(H_2O)_2^{2+}$ + 2AgX + $Y^{2-}$ $Y=SO_4^{2-}$ Step 3.

$PtL(H_2O)_2^{2+}$ + $Z_2$(oxalate) → PtL(oxalate) + $2Z^+$ $Z=K^+$, $Na^+$ or $H^+$ U.S. Pat. No. 5,290,961 in the name of Tanaka Kikinzoku Kogyo K. K. teaches that the abovementioned method has the disadvantage that many impurities are incorporated into the products. These impurities include unreacted $PtLX_2$, AgX and Ag+. The presence of $PtLX_2$ is attributed to its generally insoluble nature in water. As a result, large quantities of water must be used in step 2 to dissolve $PtLX_2$. This prevents the AgX, even though it is insoluble in water, from being completely removed from the solution. Variations of the above method through the use of silver oxalate are also documented in several patents (WO 2006/023154 A1, U.S. Pat. No. 5,420,319 U.S. Pat. Nos. 5,338,874 and 5,420,319, also in the name of Tanaka Kikinzoku Kogyo K. K.), teach processes for the production of oxalato(trans-l-1,2-diaminocyclohexane)platinum(II) with high optical purity which can be used as an active pharmaceutical ingredient of a carcinostatic agent. However, these processes also follow complicated multi-step pathways, making use of silver compounds which must also ultimately be removed from the process.

SUMMARY OF THE INVENTION

According to the invention there is provided a method for the preparation of platinum(II)oxalato complexes from their dihalogenoplatinum(II) precursors having either neutral monodentate or bidentate non-leaving co-ligands. Of particular interest is oxaliplatin. The method includes the step of reacting a halogenoplatinum(II) complex containing a neutral monodentate or bidentate ligand with an oxalate in a non-aqueous solvent or a mixed solvent system (by mixed solvent system is meant a solvent mixture containing a non-aqueous solvent and water), wherein the non-aqueous solvent is an alcohol.

The alcohol is any hydroxyl-containing organic molecule being primary, secondary or tertiary with respect to the substitution around the carbon atom bonded to the OH moiety, for example organic molecules having the arrangement $R_1$—$CH_2$—OH, $R_1R_2$—CH—OH or $R_1R_2R_3$—C—OH where the $R_1$ to $R_3$ are organic (alkyl or aryl). Preferably, the alcohol has 3 or more, typically 4-12, preferably 5-10 carbon atoms and is typically branched. Examples of alcohols are isoamyl alcohol (3-methyl-1-butanol), tertiary butanol (2-methyl-2-propanol) and 2-octanol (2-hydroxyoctane).

The oxalate may be a metal oxalate, typically an alkali metal oxalate such as rubidium or cesium oxalate; preferably cesium oxalate.

The oxalate is preferably an organic oxalate salt such as a tetraalkyl or arylammonium compound, for example a tetraethylammonium, tetrapropylammonium, tetrabutylammonium or tetraphenylphosphonium oxalate, preferably tetrabutylammonium oxalate. By "organic oxalate salt" is meant an oxalate salt where the cation is organic.

In accordance with a preferred embodiment of the invention, an aqueous solution of an organic oxalate salt is prepared by dissolving oxalic acid in a solution of the hydroxide salt of the desired organic cation, preferably tetrabutylammonium hydroxide. A cis-bis-halogenoplatinum(II) compound containing a neutral monodentate or bidentate ligand, typically trans-l-1,2-diaminocyclohexane, and where the halogen is preferably chloride, is added to the solution, followed by the addition of an alcohol to form a mixed solvent system in which the cis-bis-halogenoplatinum(II) compound is replaced by an oxalatoplatinum(II) complex product, such as oxaliplatin, which precipitates out of solution.

The ratio of alcohol:water (v/v) in the mixed solvent system may be from 70:30 to 99:1, more preferably 80:20 to 99:1, most preferably 90:10.

Preferably, the halogenoplatinum(II) complex containing neutral monodentate or bidentate ligands is reacted with the oxalate at a molar ratio of greater than 1:1, typically between 1:1 to 1:15, preferably between 1:1 and 1:5, most preferably from 1:2 to 1:2.5.

The reaction may be performed at a temperature in the range from 70 to 110° C., preferably from 75 to 95° C., most preferably from 85 to 90° C.

The amount of halogenoplatinum(II) complex containing a neutral bidentate ligand in the solvent system may be more than 5 g/L, preferably more than 10 g/L, more preferably more than 20 g/L, more preferably more than 30 g/L, most preferably more than 40 g/L.

The oxalatoplatinum(II) complex product may be purified by dissolving the product in heated water. When approximately 95% of the product is in solution it is filtered and the resulting liquor is cooled to form precipitated crystals of the product which may be collected by suction filtration, washed with several small volumes of dry acetone and dried to provide a first crop of product. A subsequent solid crop of product may be obtained by concentrating the mother liquor under vacuum and washing with dmf followed by washing and drying with acetone. The subsequent crop is combined with the first crop to provide a final purified product.

The halogen in the halogenoplatinum(II) complex may be Cl, Br or I, preferably Cl.

Advantageously, the halogenoplatinum(II) complex containing a neutral bidentate ligand is optically pure.

The neutral bidentate ligand in the halogenoplatinum(II) complex may be an amine such as 1,2-diaminocyclohexane.

The halogenoplatinum(II) complex is preferably bis-chloro-(trans-l-1,2-diaminocyclohexane)platinum(II), most preferably cis-bis-chloro(trans-l-1,2-diaminocyclohexane) platinum(II).

DETAILED DESCRIPTION OF EMBODIMENTS

PCT Patent Publication no. WO 2006/024897, the content of which is incorporated herein by reference, describes a method for the preparation of a platinum(II) complex containing a neutral bidentate ligand, such as oxaliplatin. The method includes the step of reacting a halogenoplatinum(II) complex containing a neutral bidentate ligand with an oxalate salt in an aqueous solvent (water), a non-aqueous solvent or a mixed solvent system. The non-aqueous solvent described is an amide, typically dimethylformamide (dmf). In accordance with the present invention, it has been found that the use of an alcohol as the non-aqueous solvent has unexpected advantages over dmf.

Optically pure trans-l-1,2-diaminocyclohexane is used to prepare an optically pure halogenoplatinum complex containing a neutral bidentate ligand in the form of cis-bis-halogeno(trans-l-1,2-diaminocyclohexane)platinum(II), from $K_2PtX_4$ where X=Cl, Br, I, preferably X=Cl.

Optically pure trans-l-1,2-diaminocyclohexane is reacted with a platinum(II) compound such as $K_2PtX_4$ where X is a halide such Cl, Br or I, typically $K_2PtCl_4$, to form cis-bis-halogeno(trans-l-1,2-diaminocyclohexane)platinum(II), typically cis-bis-chloro-(trans-l-1,2-diaminocyclohexane)platinum(II). This method is described in Inorganica Chimica Acta (1985) 108: pp 63-66 (the content of which is incorporated herein by reference).

The optically pure cis-bis-halogeno(trans-l-1,2-diaminocyclohexane)platinum(II), typically cis-bis-chloro-(trans-l-1,2-diaminocyclohexane)platinum(II), is then reacted with an oxalate salt in a non aqueous solvent or mixed solvent system (by mixed solvent system is meant a solvent mixture containing a non-aqueous solvent and water), wherein the non-aqueous solvent is an alcohol.

In a preferred embodiment of the invention, an aqueous solution of an organic oxalate salt (e.g. a tetra-alkyl or aryl ammonium compound such as tetraethyl, tetrapropyl or tetrabutylammonium oxalate) is prepared by dissolving oxalic acid in a solution of tetraalkylammonium hydroxide, and adjusting the pH to 7. The preferred organic oxalate salt is tetrabutylammonium oxalate. The cis-bis-halogeno(trans-l-1,2-diaminocyclohexane)platinum(II), where the halogen is preferably chloride (such as dichloro((1R,1R)-(−)-1,2-diaminocyclohexane)platinum(II)) is added to the solution, followed by the addition of the alcohol to provide the mixed solvent system. The alcohol may be any hydroxyl-containing organic molecule being primary, secondary or tertiary with respect to the substitution around the carbon atom bonded to the OH moiety. The alcohol may be an organic molecule having the arrangement $R_1$—$CH_2$—OH, $R_1R_2$—CH—OH or $R_1R_2R_3$—C—OH where $R_1$ to $R_3$ are organic (alkyl or aryl), most preferably an alkyl group ranging from butyl to octyl. Examples of alcohols are isoamyl alcohol (3-methyl-1-butanol), tertiary butanol (2-methyl-2-propanol) and 2-octanol (2-hydroxyoctane). The ratio of alcohol:water (v/v) in the mixed solvent system may be from 70:30 to 99:1, preferably from 80:10 to 99:1, most preferably 90:10. The cis-bis-chloro (trans-l-1,2-diaminocyclohexane)platinum(II) and oxalate salt are reacted at a molar ratio of greater than 1:1, typically between 1:1 to 1:10, preferably between 1:1 to 1:5, most preferably from 1:2 to 1:2.5. The amount of cis-bis-chloro (trans-l-1,2-diaminocyclohexane)platinum(II) to solvent may be more than 5 g/L, preferably more than 10 g/L, more preferably more than 20 g/L, more preferably more than 30 g/L, most preferably more than 40 g/L. This high ratio of cis-bis-chloro(trans-l-1,2-diaminocyclohexane)platinum(II) to solvent makes the process particularly suitable for the production of oxaliplatin on an industrial scale. The reaction mixture is stirred continuously at an elevated temperature of 70 to 110° C., preferably 75 to 95° C., most preferably 85 to 95° C. for 6-10 hrs, typically 8-10 hrs. During this time the relatively insoluble cis-bis-halogeno(trans-l-1,2-diaminocyclohexane)platinum(II) is replaced by an oxalatoplatinum(II) complex (in the preferred embodiment of the invention, white oxaliplatin) which precipitates out of solution. Thereafter, the mixture is cooled to 2-4° C., and the solids collected by suction filtration and washed with several volumes of dry acetone. An oxalatoplatinum(II) complex is recovered as a crystalline solid with a yield of up to 85%. Purification of the crystalline solid may be effected by dissolving the solid in water preheated to 70-75° C. When approximately 95% of the solid is in solution, it is filtered and the liquor cooled at 4° C. for 6-10 h. The precipitated crystals are collected by suction filtration, washed with several small volumes of dry acetone and dried at 50° C. to provide a first crop with a yield of up to 50% (based on cis-bis-halogeno(trans-l-1,2-diaminocyclohexane)platinum(II)). A subsequent crop is obtained by concentrating the mother liquor under vacuum. If the resulting solids are contaminated with small amounts of unreacted yellow cis-bis-halogeno(trans-l-1,2-diaminocyclohexane)platinum(II), the latter can be removed by careful washing with minimal volumes of dmf. The resulting solid is then washed with acetone and dried at 50° C., and the combined crops can produce an overall yield of up to 74%. Where the method is used to produce oxaliplatin, a pure white oxaliplatin product is obtained. The overall oxaliplatin product yield is approximately 74% (based on cis-bis-chloro(trans-l-1,2-diaminocyclohexane)platinum(II)) with optical purity ≧99% ee/LC and chemical purity ≧99%.

The tetraalkylammonium oxalate may be prepared by combining one molar equivalent of oxalic acid with two molar equivalents of a 40% aqueous solution of tetraalkylammonium hydroxide. The solution is stirred at room temperature until the oxalic acid is dissolved, whereafter the pH is adjusted to 7 (using the same tetraalkylammonium hydroxide solution mentioned above).

The process described above may be used to form many other platinum(II) complexes with neutral bidentate ligands (such as the neutral bidentate ligands described in WO2005/051966 and WO2006/024897, the contents of which are incorporated herein by reference), and it is possible to form platinum(II) complexes with neutral bidentate ligands that contain donor atoms other than N, typically S, for example:
neutral bidentate heterocyclic amines with an S donor atom, such as thioetherial S containing compounds of the general formula:
1-alkyl/aryl-2-alkylthioalkyl/aryl heterocyclic amines, particularly imidazoles or pyridines;
aminoalkylthioalkyl/aryl compounds;
dithioethers for example 2,5-dithiahexane.

The following 2-methylthioalkyl imidazole and pyridine neutral bidentate ligands:
Ligand (i) 1-methyl-2-methylthiomethylimidazole
Ligand (ii) 1-methyl-2-methylthioethylimidazole
Ligand (iii) 1-methyl-2-methylthiopropylimidazole
Ligand (iv) 1-butyl-2-methylthiomethylimidazole
Ligand (v) 1-butyl-2-methylthioethylimidazole
Ligand (vi) 2-methylthiomethylpyridine
Ligand (vii) 2-methylthioethylpyridine
Ligand (viii) 2-methylthiopropylpyridine
(prepared by the methods described in J G H du Preez, T I A Gerber, W Edge, V L V Mtotywa and B J A M van Brecht. Nitrogen Reagents in Metal Ion Separation. XI. The Synthesis and Extraction Behaviour of a New NS imidazole Derivative. Solv. Extr. & Ion Exch. (2001) 19(1), 143-154) (the content of which is incorporated herein by reference) may be used in the process of the invention to prepare the 2-methylthioalkyl complexes of imidazole and pyridine (i) to (v) mentioned below.

Examples of 2-methylthioalkyl complexes of imidazole prepared by the process of the invention are reflected in the structural Formula (I) below where $R_1$ and $R_2$ may be selected from alkyl (e.g. $CH_3$, $C_2H_6$ etc.) and aryl (e.g. phenyl) groups. Typical 2-methylthioalkyl complexes of imidazole are complexes (i) to (v) below:

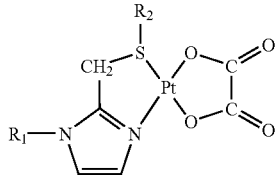

Formula (I)

Complex (i) $R_1=CH_3$ $R_2=CH_3$
Complex (ii) $R_1=CH_3$ $R_2=C_2H_5$
Complex (iii) $R_1=CH_3$ $R_2=C_3H_7$
Complex (iv) $R_1=C_4H_9$ $R_2=CH_3$
Complex (v) $R_1=C_4H_9$ $R_2=C_2H_5$ The chemical names for the complexes (i) to (v) are:
Complex (i) oxalato(1-methyl-2-methylthiomethylimidazole)platinum(II)
Complex (ii) oxalato(1-methyl-2-methylthioethylimidazole)platinum(II)
Complex (iii) oxalato(1-methyl-2-methylthiopropylimidazole)platinum(II)
Complex (iv) oxalato(1-butyl-2-methylthiomethylimidazole)platinum(II)
Complex (v) oxalato(1-butyl-2-methylthioethylimidazole)platinum(II).

Examples of 2-methylthioalkyl complexes of pyridine that may be prepared by the process of the invention are reflected in the structural Formula (II) below where $R_2$ may be selected from alkyl (e.g. $CH_3$, $C_2H_5$ etc.) and aryl (e.g. phenyl) groups. Typical 2-methylthioalkyl complexes of pyridine are compounds (vi) to (viii) below:

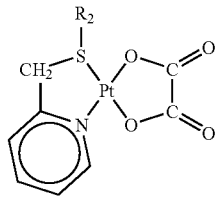

Formula (II)

Complex (vi) $R_2=CH_3$
Complex (vii) $R_2=C_2H_5$
Complex (viii) $R_2=C_3H_7$

The chemical names for the complexes (vi) to (viii) are:
Complex (vi) oxalato(2-methylthiomethylpyridine)platinum(II)
Complex (vii) oxalato(2-methylthioethylpyridine)platinum(II)
Complex (viii) oxalato(2-methylthiopropylpyridine)platinum(II).

The following ligands:
Ligand (ix) 1-amino-2-thiomethylethane
Ligand (x) 1-amino-2-thioethylethane
may be used to prepare the following aliphatic aminothioether complexes of Pt(II)oxalate:
Complex (ix) oxalato(1-amino-2-thiomethylethane)platinum(II)
Complex (x) oxalato(1-amino-2-thioethylethane)platinum(II).

Other halogenoplatinum(II) complexes which may be used in the methods of this invention include halogenoplatinum(II) complexes having a neutral bidentate ligand that contains donor atoms other than N, typically S, for example:
neutral bidentate heterocyclic amines with an S donor atom, such as thioetherial S containing compounds of the general formula:
1-alkyl/aryl-2-alkylthioalkyl/aryl heterocyclic amines, particularly imidazoles or pyridines;
aminoalkylthioalkyl/aryl compounds;
dithioethers for example 2,5-dithiahexane;
The neutral bidentate ligand may be selected from any of ligands i) to x) above.

The halogenoplatinum(II) complex may be prepared by reacting a platinum(II) compound such as $K_2PtX_4$, where X is a halide such Cl, Br or I, preferably Cl, with a suitable neutral bidentate ligand. Typical halogenoplatinum(II) complexes so formed are reflected in the structural Formula (III) below where $R_1$ and $R_2$ may be selected from alkyl (e.g. $CH_3$, $C_2H_5$ etc.) and aryl (e.g. phenyl) groups.

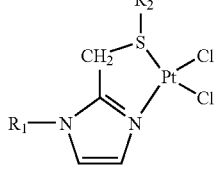

Formula (III)

Complex (xi) $R_1=CH_3$ $R_2=CH_3$
Complex (xii) $R_1=CH_3$ $R_2=C_2H_5$
Complex (xiii) $R_1=CH_3$ $R_2=C_3H_7$
Complex (xiv) $R_1=C_4H_9$ $R_2=CH_3$
Complex (xv) $R_1=C_4H_9$ $R_2=C_2H_5$ The chemical names for the complexes (xi) to (xv) are:
Complex (xi) bis-chloro-(1-methyl-2-methylthiomethylimidazole)platinum(II)
Complex (xii) bis-chloro-(1-methyl-2-methylthioethylimidazole)platinum(II)
Complex (xiii) bis-chloro-(1-methyl-2-methylthiopropylimidazole)platinum(II)
Complex (xiv) bis-chloro-(1-butyl-2-methylthiomethylimidazole)platinum(II)
Complex (xv) bis-chloro-(1-butyl-2-methylthioethylimidazole)platinum(II).

Other halogenoplatinum(II) complexes which may be used in the methods of this invention include halogenoplatinum(II) complexes having neutral monodentate ligands, such as cis-dichlorodiamminoplatinum(II) (cisplatin). cis-Dichlorodiamminoplatinum(II), tetrabutylammonium oxalate and a mixed solvent system containing an alcohol such as isoamyl alcohol may be stirred vigorously at 75° C. for 10 h to produce a white precipitate of cis-diamminooxalatoplatinum(II). In the reaction mixture, the ratio of cisplatin:oxalate may be 1:2.5, the ratio of alcohol:water may be 95:5 and the amount of cisplatin in the reaction mixture 6.7 g/L.

The use of an alcohol as or as part of the solvent in accordance with the present invention, instead of dmf, has the following advantages:

(i) The yield of crude product is higher in the alcohol system, up to 85% as compared to 67% in the dmf system.
(ii) The alcohol system makes use of a single reaction of 8 h which produces the crude white crystals directly. These are washed and recrystallized. The dmf system is multi-stepped after the initial reaction of 6-10 hours, the dmf solvent is evaporated and the residue dissolved in heated water and filtered. The water is evaporated and the resulting residue treated with ethanol to remove residual tetrabutylammonium oxalate and derivatives thereof. The solids are recovered by centrifusion and must then be washed with dmf before a white oxaliplatin product can be obtained. Thus a complex time-consuming procedure.
(iii) The insolubility of the oxaliplatin in the alcohol system results in a progressive crystallization of a very readily filtrationable product which also drives the reaction closer to completion and at the same time avoids decomposition of the product.
(iv) The smaller donor number (weaker donicity) of the alcohol limits the formation of intermediate solvated products via coordination. Evidence for the formation of these was found in the dmf solvent system.
(v) The yield of the pure product is significantly higher in the alcohol system, viz. 72% as compared to 30% to 36% in the dmf system (see Examples 3 and 6 of WO 2006/024897).

The invention will now be described in more detail with reference to the following non-limiting examples.

Example 1

An aqueous solution of tetrabutylammonium oxalate, prepared by dissolving oxalic acid (8.29 g, 0.0658 mol) in a 40% solution of tetrabutylammonium hydroxide (approx. 88 mL, 0.131 mol) and adjusting the pH to 7, was added to solid dichloro((trans-l-1,2-diaminocyclohexane)platinum(II)) (10 g, 0.0263 mol) followed by 1.1 L of isoamyl alcohol (3-methyl-1-butanol). In this mixture, the molar ratio of platinum (II) compound:oxalate was 1:2.5, the ratio of alcohol:water (v/v) 95:5, and the amount of dichloro((trans-l-1,2-diaminocyclohexane)platinum(II) in the solvent reaction mixture was 8.3 g/L.

The mixture was stirred for 8 h whilst its internal temperature was thermostatically maintained at 85° C. During this time the relatively insoluble dichloro(trans-l-1,2-diaminocyclohexane)platinum(II) was replaced by white oxaliplatin which precipitated out of solution.

Thereafter, the mixture was cooled at 4° C., the solids collected by suction filtration and washed with several volumes of dry acetone. The relatively pure oxaliplatin was recovered with a yield of 83% (8.71 g) as an off-white crystalline solid.

Purification was effected by dissolving the above solids in 500 mL water preheated to 70-75° C. When approximately 95% of the material was in solution, it was filtered and the liquor cooled at 4° C. for 6-10 h. The precipitated white crystals were collected by suction filtration, washed with several small volumes of dry acetone and dried at 50° C. Yield=47% (4.9 g). (1st crop).

The subsequent crop was obtained by concentrating the mother liquor under vacuum. The resulting solids had a yellow colouration due to contamination with small amounts of unreacted dichloro(trans-l-1,2-diaminocyclohexane)platinum(II).

The latter was removed by careful washing with minimal volumes of dmf until the yellow colour was removed. The white solids were then washed with acetone and dried at 50° C.

The combined crops (1 & 2) totaled 7.47 g (72% overall yield).

Example 2

PtdachCl$_2$ (50 g, 0.132 mol), tetrabutylammonium oxalate (274 ml, 0.96 M) (prepared by dissolving 33.2 g oxalic acid in 0.35 L 40% tetrabutylammonium hydroxide and evaporating 110 mL water), and isoamyl alcohol (925 ml) were charged into a reactor. In this mixture the molar ratio of PtdachCl$_2$:oxalate was 1:2, the ratio alcohol:water (v/v) was 90:10 and the amount of PtdachCl$_2$ in the reaction mixture was 42 g/L. The mixture was heated to an internal temperature of 88° C. for 8-10 h accompanied by vigorous stirring. During this time the relatively insoluble PtdachCl$_2$ was replaced by white oxaliplatin which precipitated out of the reaction mixture.

After reaction, the mixture was cooled to an internal temperature of 2-4° C. for 1-2 h, whereafter the precipitate was recovered via suction filtration on a sintered glass filter. The precipitate was washed with several volumes of dry acetone and dried. A crude yield of 86% (45 g) oxaliplatin (relative to PtdachCl$_2$) was obtained.

Purification was effected by dissolving the crude solids in 2.5 L water at a temperature of 75° C. When approximately 95% of the material was in solution, it was filtered and the liquor cooled at 4° C. for 6-10 h. The precipitated crystals were collected via suction filtration and washed with dry acetone. Yield=28 g (50% relative to PtdachCl$_2$).

A subsequent crop was obtained by concentrating the mother liquor under vacuum at 60° C. The precipitated white solids were collected, washed with dry acetone and dried under vacuum at 60° C.

The combined yield of crops was 65% (relative to PtdachCl$_2$).

Example 3

PtdachCl$_2$ (10 g, 0.026 mol), tetrabutylammonium oxalate (0.066 mol) (prepared by dissolving 8.3 g oxalic acid in 88 ml of a 40% wt solution of tetrabutylammonium hydroxide and adjusting the pH to 7) and 520 ml 2-octanol were stirred together at 85° C. for 10 h. In this mixture the molar ratio of PtdachCl$_2$:oxalate was 1:2.5, the ratio of alcohol:water (v/v) was 90:10 and the amount of PtdachCl$_2$ in the reaction mixture was 16 g/L.

During this time the relatively insoluble PtdachCl$_2$ was replaced by white oxaliplatin which precipitated out of the reaction mixture. After reaction, the mixture was cooled at 4° C., the solids collected by suction filtration and washed with several volumes of dry acetone. The relatively pure oxaliplatin was recovered with a yield of 80% (relative to PtdachCl$_2$) as an off-white crystalline solid.

Purification was effected by dissolving the above solids in 450 ml water preheated to 75° C. When approximately 95% of the material was in solution, it was filtered and the liquor cooled at 4° C. for 6-10 h. The precipitated white crystals were collected by suction filtration, washed with several small volumes of dry acetone and dried at 50° C. Yield=50% (relative to PtdachCl$_2$).

A subsequent crop was obtained by concentrating the mother liquor under vacuum at 60° C.

The combined crops (1 & 2) totaled 7.3 g (70% relative to PtdachCl$_2$).

Example 4 cis-Dichlorodiamminoplatinum(II) (cisplatin) (10 g, 0.033 mol), tetrabutylammonium oxalate (0.083 mol) (prepared by dissolving 10.5 g oxalic acid in 112 ml 40% tetrabutylammonium hydroxide solution and adjusting the pH to 7) and 1.4 L isoamyl alcohol were stirred vigorously at 75° C. for 10 h. In this mixture the ratio of cisplatin:oxalate was 1:2.5, the ratio of alcohol:water was 95:5 and the amount of cisplatin in the reaction mixture 6.7 g/L. During this time, a white precipitate of cis-diamminooxalatoplatinum(II) formed. After reaction, the white solids were recovered by filtration at a crude yield of 96%.

Purification was effected by recrystallization from water at 75° C. to furnish 5 g of pure cis-diamminooxalatoplatinum (II) (47% yield relative to cisplatin).

The invention claimed is:

1. A method for the preparation of a platinum(II) complex containing neutral monodentate or bidentate ligands, the method including the step of reacting a halogenoplatinum(II) complex containing neutral monodentate or bidentate ligands with an oxalate in a non-aqueous solvent or a mixed solvent system, wherein the non-aqueous solvent is an alcohol.

2. The method according to claim 1, wherein the alcohol is an organic molecule having the arrangement R$_1$—CH$_2$—OH, R$_1$R$_2$—CH—OH or R$_1$R$_2$R$_3$—C—OH where the R$_1$ to R$_3$ are organic alkyl or aryl groups.

3. The method according to claim 1, wherein the alcohol has 3 or more carbon atoms.

4. The method according to claim 3, wherein the alcohol has 4-12 carbon atoms.

5. The method according to claim 4, wherein the alcohol has 5-10 carbon atoms.

6. The method according to claim 1, wherein the alcohol is 3-methyl-1-butanol (isoamyl alcohol).

7. The method according to claim 1, wherein the alcohol is 2-methyl-2-propanol (tertiary butanol).

8. The method according to claim 1, wherein the alcohol is 2-hydroxyoctane (2-octanol).

9. The method according to claim 1, wherein the oxalate is an organic oxalate salt.

10. The method according to claim 9, wherein the organic oxalate is a tetraalkyl or arylammonium compound.

11. The method according to claim 10, wherein the organic oxalate is a tetraethylammonium, tetrapropylammonium, tetrabutylammonium or tetraphenylphosphonium oxalate.

12. The method according to claim 11, wherein the organic oxalate is tetrabutylammonium oxalate.

13. The method according to claim 1, wherein the solvent is a mixed solvent system.

14. The method according to claim 13, wherein the ratio of alcohol:water (v/v) in the mixed solvent system is from 70:30 to 99:1.

15. The method according to claim 14, wherein the ratio of alcohol:water (v/v) in the mixed solvent system is from 80:20 to 99:1.

16. The method according to claim 15, wherein the ratio of alcohol:water (v/v) in the mixed solvent system is 90:10.

17. The method according to claim 1, wherein the halogenoplatinum(II) complex containing neutral monodentate or bidentate ligands is reacted with the oxalate at a molar ratio of greater than 1:1.

18. The method according to claim 17, wherein the halogenoplatinum(II) complex containing neutral monodentate or bidentate ligands is reacted with the oxalate at a molar ratio of between 1:1 to 1:15.

19. The method according to claim 18, wherein the halogenoplatinum(II) complex containing neutral monodentate or bidentate ligands is reacted with the oxalate at a molar ratio of between 1:1 to 1:5.

20. The method according to claim 19, wherein the halogenoplatinum(II) complex containing neutral monodentate or bidentate ligands is reacted with the oxalate at a molar ratio of from 1:2 to 1:2.5.

21. The method according to claim 1, wherein the reaction is carried at a temperature in the range from 70 to 110° C.

22. The method according to claim 21, wherein the reaction is carried out at a temperature in the range of from 75 to 95° C.

23. The method according to claim 22, wherein the reaction is carried out at a temperature in the range of from 85 to 95° C.

24. The method according to claim 1, wherein the amount of halogenoplatinum(II) complex containing neutral monodentate or bidentate ligands in the solvent system is more than 5 g/L.

25. The method according to claim 24, wherein the amount of halogenoplatinum(II) complex containing neutral monodentate or bidentate ligands in the solvent system is more than 10 g/L.

26. The method according to claim 25, wherein the amount of halogenoplatinum(II) complex containing neutral monodentate or bidentate ligands in the solvent system is more than 30 g/L.

27. The method according to claim 26, wherein the amount of halogenoplatinum(II) complex containing neutral monodentate or bidentate ligands in the solvent system is more than 40 g/L.

28. The method according to claim 1, wherein the halogen in the halogenoplatinum(II) complex is Cl, Br or I.

29. The method according to claim 28, wherein the halogen is Cl.

30. The method according to claim 1, wherein the halogenoplatinum(II) complex containing neutral monodentate or bidentate ligands is optically pure.

31. The method according to claim 1, wherein the ligand in the halogenoplatinum(II) complex is a neutral bidentate ligand.

32. The method according to claim 31, wherein the neutral bidentate ligand in the halogenoplatinum(II) complex is an amine.

33. The method according to claim 32, wherein the neutral bidentate ligand in the halogenoplatinum(II) complex is 1,2-diaminocyclohexane.

34. The method according to claim 1, wherein the ligand in the halogenoplatinum(II) complex is a neutral monodentate ligand.

35. The method according to claim 34, wherein the neutral monodentate ligand in the halogenoplatinum(II) complex is an amine.

36. The method according to claim 35, wherein the neutral monodentate ligand in the halogenoplatinum(II) complex is cis-dichlorodiamminoplatinum(II).

37. The method according to claim 1, wherein the halogenoplatinum(II) complex is bis-chloro-(trans-l-1,2-diaminocyclohexane)platinum(II).

38. The method according to claim 37, wherein the halogenoplatinum(II) complex is cis-bis-chloro(trans-l-1,2-diaminocyclohexane)platinum(II).

* * * * *